United States Patent [19]

Arth et al.

[11] 4,092,413

[45] May 30, 1978

[54] ANTIANDROGENS AS PLATELET AGGREGATION INHIBITORS

[75] Inventors: Glen E. Arth, Cranford, N.J.; Sumner Wood, Jr., deceased, late of Cranford, by Linda S. Windsor Wood, administratrix

[73] Assignee: Merck & Co., Inc., Rahway, N.J.

[21] Appl. No.: 809,512

[22] Filed: Jun. 23, 1977

Related U.S. Application Data

[63] Continuation of Ser. No. 446,171, Feb. 28, 1974, abandoned.

[51] Int. Cl.$^2$ .................. C07J 71/00; A61K 31/58
[52] U.S. Cl. ..................... 424/241; 260/239.57; 260/397.3; 260/397.4; 260/397.1

[58] Field of Search ............ 424/241; 260/239.57, 260/397.3, 397.4, 397.1

[56] References Cited

U.S. PATENT DOCUMENTS 3,380,886  4/1968  Campbell .................. 424/243

*Primary Examiner*—Elbert L. Roberts
*Attorney, Agent, or Firm*—Henry H. Bassford, Jr.; J. Jerome Behan; Rudolph J. Anderson, Jr.

[57] ABSTRACT

The invention disclosed herein relates to antiandrogenic compositions active, in vivo, as inhibitors of the aggregation of mammalian blood platelets, and to the method of preventing, arresting or reversing blood platelet aggregation by the administration to mammals of such antiandrogenic compositions.

10 Claims, No Drawings

ANTIANDROGENS AS PLATELET AGGREGATION INHIBITORS

This is a continuation of application Ser. No. 446,171, filed Feb. 28, 1974, now abandoned.

The present invention is concerned generally with novel methods of inhibiting the aggregation of blood platelets in mammals, and with novel compositions which achieve such inhibition. More particularly, it relates to compositions having antiandrogenic action, and to the inhibition of such platelet aggregation by the administration of these antiandrogenic compositions to mammals. Platelet aggregation is known to be involved in atheroscleosis and concomitant thrombotic processes, and inhibition of platelet aggregation in vivo is thus of value in the prevention, arrest or minimization of thrombi of the coronary or carotid arterial systems and their branches, as well as in other vascular beds such as the lungs, pelvis or extremities. The discovery of this unique class of antiandrogenic blood-platelet-aggregation-inhibitors was indeed surprising since, in conventional in vitro test systems where blood plasma-containing platelets is subjected to the aggregating action of adenosine diphosphate (hereinafter called ADP) in the presence of the test compound, the antiandrogenic compositions of this invention are completely inactive in preventing or inhibiting platelet aggregation. Only when such compounds are administered to an intact mammal, and the blood plasma collected from said mammal subjected to the action of ADP, is inhibition of platelet aggregation observed. Moreover, these novel antiandrogenic blood-aggregation-inhibiting compositions, when so administered to an intact mammal, and the blood plasma subjected to the action of ADP, not only result in inhibition of blood platelet aggregation, but in fact exert a remarkable disaggregating affect on aggregated blood platelets.

These antiandrogenic compositions, characterized as inhibiting blood platelet-aggregation, include, in admixture with a pharmacologically acceptable carrier, compounds which can deprive the mammalian system of a physiological characteristic referred to as androgen expression, as for example (a) compounds which inhibit the biosynthesis of androgens from their precursors such as 17β-ureido-androst-4-ene-3-one; 17β-ureido-androsta-1,4-diene-3-one; 17β-acylamido-androst-4-ene-3-one; 17β-formamidoandrost-4-ene-3-one; 17β-acetamido-androst-4-ene-3-one; 17β-acylamido-androst-1,4-diene-3-one; 17β-formamido-androsta-1,4-diene-3-one; 17β-acetamido-androsta-1,4-diene-3-one, and the like, (b) compounds which inhibit the conversion of one androgen (i.e. testosterone) to another such as 17β-carboxy-androst-4-ene-3-one, 17β-carboalkoxy-androst-4-ene-3-one, 17β-carbomethoxy-androst-4-ene-3-one, 20-spirox-4-ene-3-one; 19-nor-20-spirox-4-ene-3-one, and the like; and (c) compounds which antagonize the action of some or all of the natural mammalian androgens (e.g. testosterone, 17β-hydroxy-5α-androstan-3-one (DHT), and 3 and 17 oxidation and reduction products of DHT), such as the androgen antagonists 1,2α-methylene-6,7α-difluoromethylene-20-spirox-4-ene-3-one; 6-chloro-1,2α-methylene-4,6-pregnadiene-17α-ol-3,20-dione acetate; 17α-methyl-B-nor-testosterone; 6,17α-dimethylpregna-4,6-diene-3,20-dione, N-isobutyryl-4-nitro-3-trifluoromethyl-aniline. and N-[(3,5-dimethyl-4-oxazolyl)-methyl]-phthalimide, and the like.

The presently invented antiandrogenic compositions, containing these androgen antagonists and inhibitors of androgen bisynthesis or interconversion, comprise the steroid compound in admixture with a pharmacologically-acceptable solid or liquid carrier, and are prepared for administration in conventional dosage forms such as pills, tablets, capsules, syrups for oral use, or in a liquid form adapted for administration of steroid compounds by injection; microcrystalline aqueous suspensions or oil-in-water emulsions can be prepared for parenteral dosage. Dosage levels of these antiandrogenic compositions may vary depending on the blood platelet-aggregation-inhibiting activity of the antiandrogenic compound contained in such composition, but such compositions are ordinarily administered at a level to provide a daily dosage of about 0.1 - 20 mg. of the antiandrogenic compound per kilogram of body weight.

Test Procedure for Platelet Aggregation

The blood-platelet-aggregation-inhibiting action of these antiandrogenic compositions is demonstrated by the following test procedure: platelet-rich plasma is prepared by differential centrifugation (at 375 G) for 2–4 minutes of whole citrated* blood from control mammals, and from those treated with antiandrogenic compositions. [An aliquot of the platelet-rich plasma is centrifuged (at 10,000 G) for 5–10 minutes to prepare plasma substantially free of platelets for calibration of the zero setting of the aggregometer**]. A mixture of 0.4 ml. of platelet-rich plasma and 0.1 ml. of physiological saline solution containing 60 mg. $Ca^{++}$ ion per 100 ml. is stirred in the aggregometer at 37° C. for approximately 1 minute. About 0.1 ml. of a $10^{-4}$ molar solution of ADP (adenosine diphosphate) is added, and the course of the resulting platelet aggregation, and disaggregation, as indicated by changes in light transmission in the aggregometer, is observed for the plasma from both the control and treated mammals. These observations show that, for blood plasma derived from mammals treated with antiandrogenic compositions, and in particular androgen-biosynthesis inhibitors such as 17β-ureido-androsta-1,4-diene-3-one, inhibitors of androgen-interconversion such as 17β-carboxy-androst-4-ene-3-one, and androgen-antagonists such as 6-chloro-1,2α-methylene-4,6-pregnadiene-17α-ol-3,20-dione acetate, and 1,2α-methylene-6,7α-difluoromethylene-20-spirox-4-ene-3-one, the rates and extent of platelet-aggregation are both reduced approximately 40% as compared with the platelet-aggregation in plasma obtained from the control mammals.

* Sodium citrate, which is a calcium-sequestrant, acts as a blood-anticoagulant.
** The aggregometer determines the extent of platelet aggregation by measuring light transmitted by the plasma sample; the aggregometer used is manufactured by CHRONO-log Corp., Ardmore, Pa.

The following examples illustrate methods of carrying out the present invention but it is to be understood that these examples are given for purpose of illustration and not of limitation.

EXAMPLE 1

The effect on platelet aggregation, resulting from oral administration of an anti-androgenic composition containing the androgen-biosynthesis inhibitor, 17β-ureido-androsta-1,4-diene-3-one, was studied in six fasting male rabbits. The said composition consisted of a solution of 17β-ureido-androsta-1,4-diene-3-one dissolved in sesame oil at a level of 10 milligrams of steroid per milliliter of sesame oil.

Control blood samples were taken from each rabbit, and each rabbit then received orally an amount of said solution sufficient to provide 10 milligrams of 17β-ureido-androsta-1,4-diene-3-one per kilogram of body weight. Blood samples were then taken from each of the treated rabbits at intervals and, in accordance with the foregoing test procedure, platelet-rich plasma was prepared from each sample, the platelet count was determined*, and the ADP-induced platelet aggregation was measured using the aggregometer for each of the control and treated samples. The results, which were plotted automatically by the aggregometer, showed that the rate and extent of platelet aggregation in the plasma from the rabbits treated with 10 milligrams of 17β-ureido-androsta-1,4-diene-3-one per kilogram of body weight, were both reduced approximately 40% as compared with platelets in the control plasma.

* The platelet count remained constant for all samples thus making valid the optical density measurements.

EXAMPLE 2

The effect on platelet aggregation, resulting from oral administration of an antiandrogenic composition containing the androgen-interconversion inhibitor, 17β-carboxy-androst-4-ene-3-one, was studied in five fasting male rabbits. The said composition consisted of a solution of 17β-carboxy-androst-4-ene-3-one dissolved in sesame oil at a level of 20 milligrams of steroid per milliliter of sesame oil.

Control blood samples were taken from each rabbit, and each rabbit then received orally an amount of said solution sufficient to provide 20 milligrams of 17β-carboxy-androst-4-ene-3-one per kilogram of body weight. Blood samples were then taken from each of the treated rabbits at intervals and, in accordance with the foregoing test procedure, platelet-rich plasma was prepared from each sample, the platelet count was determined (such count remained constant for all samples thus making valid the optical density measurements) and the ADP-induced platelet aggregation was measured using the aggregometer for each of the control and treated samples. The results, which were plotted automatically by the aggregometer showed that the rate and extent of platelet aggregation in the plasma from the rabbits treated with 20 milligrams of 17β-carboxy-androst-4-ene-3-one per kilogram of body weight, were both reduced approximately 40% as compared with platelets in the control plasma.

EXAMPLE 3

The effect on platelet aggregation, resulting from oral administration of an antiandrogenic composition containing the androgen antagonist, 1,2α-methylene-6,7α-difluoromethylene-20-spirox-4-ene-3-one, was studied in five fasting male rabbits. The said composition consisted of a solution of 1,2α-methylene-6,7α-difluoromethylene-20-spirox-4-ene-3-one dissolved in sesame oil at a level of 10 milligrams of steroid per milliliter of sesame oil.

Control blood samples were taken from each rabbit, and each rabbit then received orally an amount of said solution sufficient to provide 10 milligrams of 1,2α-methylene-6,7α-difluoromethylene-20-spirox-4-ene-3-one per kilogram of body weight. Blood samples were then taken from each of the treated rabbits at intervals and, in accordance with the foregoing test procedure, platelet-rich plasma was prepared from each sample, the platelet count was determined (such count remained constant for all samples thus making valid the optical density measurements), and the ADP-induced platelet aggregation was measured using the aggregometer for each of the control and treated samples. The results, which were plotted automatically by the aggregometer, showed that the rate and extent of platelet aggregation in the plasma from the rabbits treated with 10 milligrams of 1,2α-methylene-6,7α-difluoromethylene-20-spirox-4-ene-3-one per kilogram of body weight, were both reduced approximately 40% as compared with platelets in the control plasma.

Various changes and modifications may be made in carrying out the present invention without departing from the spirit and scope thereof. Insofar as these changes and modifications are within the purview of the annexed claims, they are to be considered as part of our invention.

What is claimed is:

1. The method of inhibitng the aggregation of blood platelets in a mammal which comprises administering to said mammal a composition comprising an antiandrogenic compound which is an inhibitor of the biosynthesis or interconversion of androgens in admixture with a pharmacologically acceptable carrier, wherein said composition is in dosage unit form adapted for oral or injection administration to mammals, and contains an amount of the said inhibitor sufficient to provide a dosage level of about 0.1 – 20 milligrams of inhibitor per kilogram of body weight of said mammal.

2. The method of inhibiting aggregation of blood platelets in a mammal which comprises administering to said mammal a composition comprising an anti-androgenic compound in admixture with a pharmacologically acceptable carrier, wherein the anti-androgenic compound is the androgen-biosynthesis inhibitor 17β-ureido-androsta-1,4-diene-3-one.

3. The method of inhibiting the aggregation of blood platelets in a mammal which comprises administering to said mammal a composition comprising an anti-androgenic compound in admixture with a pharmacologically acceptable carrier, wherein the anti-androgenic compound is the androgen-biosynthesis inhibitor 17β-formamido-androsta-1,4-diene-3-one.

4. The method of inhibiting the aggregation of blood platelets in a mammal which comprises administering to said mammal a composition comprising an anti-androgenic compound in admixture with a pharmacologically acceptable carrier, wherein the anti-androgenic compound is the androgen-interconversion-inhibitor 17β-carboxy-androst-4-ene-3-one.

5. The method of inhibiting the aggregation of blood platelets in a mammal which comprises administering to said mammal a composition comprising an anti-androgenic compound in admixture with a pharmacologically acceptable carrier, wherein the anti-androgenic compound is the androgen antagonist 1,2α-methylene-6,7α-difluoromethylene-20-spirox-4-ene-3-one.

6. The method of inhibiting the aggregation of blood platelets in a mammal which comprises administering to said mammal a composition comprising an anti-androgenic compound in admixture with a pharmacologically acceptable carrier, wherein the anti-androgenic compound is the androgen antagonist 6-chloro-1,2α-methylene-4,6-pregnadiene-17α-ol-3,20-dione acetate.

7. A composition adapted for oral or injection administration to mammals, and characterized as inhibiting the aggregation of blood platelets in the blood plasma of such mammals, which comprises an anti-androgenic compound which is an inhibitor of the biosynthesis of interconversion of androgens in admixture with a pharmacologically acceptable carrier, said composition being in dosage unit form and adapted for oral or injection administration, and containing an amount of the said inhibitor sufficient to provide a dosage level of about 0.1 – 20 milligrams of inhibitor per kilogram of body weight of said mammal.

8. A composition adapted for oral or injection administration to mammals, and characterized as inhibiting the aggregation of blood platelets in the blood plasma of such mammals, which comprises 17β-ureido-androsta-1,4-diene-3-one in admixture with a pharmacologically acceptable carrier, said composition being in dosage unit form and adapted for oral or injection administration, and containing an amount of the 17β-ureido-androsta-1,4-diene-3-one sufficient to provide a dosage level of about 0.1 – 20 milligrams of said 17β-ureido-androsta-1,4-diene-3-one per kilogram of body weight of said mammal.

9. A composition adapted for oral or injection administration to mammals, and characterized as inhibiting the aggregation of blood platelets in the blood plasma of such mammals, which comprises 17β-carboxy-androst-4-ene-3-one in admixture with a pharmacologically acceptable carrier, said composition being in dosage unit form and adapted for oral or injection administration, and containing an amount of the 17β-carboxy-androst-4-ene-3-one sufficient to provide a dosage level of about 0.1 – 20 milligrams of said 17β-carboxy-androst-4-ene-3-one per kilogram of body weight of said mammal.

10. A composition adapted for oral or injection administration to mammals, and characterized as inhibiting the aggregation of blood platelets in the blood plasma of such mammals, which comprises 1,2α-methylene-6,7α-difluoromethylene-20-spirox-4-ene-3-one in admixture with a pharmacologically acceptable carrier, said composition being in dosage unit form and adapted for oral or injection administration, and containing an amount of the 1,2α-methylene-6,7α-difluoromethylene-20-spirox-4-ene-3-one sufficient to provide a dosage level of about 0.1 – 20 milligrams of said 1,2α-methylene-6,7α-difluoromethylene-20-spirox-4-ene-3-one per kilogram of body weight of said mammal.

* * * * *